United States Patent
Hibl

[11] Patent Number: 5,817,010
[45] Date of Patent: Oct. 6, 1998

[54] DISPOSABLE SENSOR HOLDER

[75] Inventor: Mark Hibl, Louisville, Colo.

[73] Assignee: Ohmeda Inc., Liberty Corner, N.J.

[21] Appl. No.: 824,107

[22] Filed: Mar. 25, 1997

[51] Int. Cl.[6] ..................................................... A61B 5/00
[52] U.S. Cl. ............................................................. 600/344
[58] Field of Search ..................................... 600/310, 311, 600/322, 323, 324, 326, 340, 344, 473, 476

[56] References Cited

U.S. PATENT DOCUMENTS

| | | | |
|---|---|---|---|
| 4,079,765 | 3/1978 | Hatayan | 145/46 |
| 4,334,544 | 6/1982 | Hill et al. | 128/664 |
| 4,685,464 | 8/1987 | Goldberger et al. | 128/633 |
| 4,830,014 | 5/1989 | Goodman et al. | 128/665 |
| 5,094,240 | 3/1992 | Muz | 128/633 |
| 5,170,786 | 12/1992 | Thomas et al. | 128/633 |
| 5,188,108 | 2/1993 | Secker | 128/633 |
| 5,209,230 | 5/1993 | Swedlow et al. | 128/633 |
| 5,247,931 | 9/1993 | Norwood | 128/633 |
| 5,311,865 | 5/1994 | Mayeux | 600/323 |
| 5,313,940 | 5/1994 | Fuse et al. | 128/633 |
| 5,337,744 | 8/1994 | Branigan | 128/633 |
| 5,413,099 | 5/1995 | Schmidt et al. | 600/310 |
| 5,414,911 | 5/1995 | Adams | 24/545 |
| 5,437,275 | 8/1995 | Amundsen et al. | 600/323 |
| 5,511,546 | 4/1996 | Hon | 128/633 |

Primary Examiner—John P. Lacyk
Assistant Examiner—Eric F. Winaker
Attorney, Agent, or Firm—Roger M. Rathbun

[57] ABSTRACT

The present invention provides an oximeter sensor holder that includes first and second lateral members for receiving the sensor, a living hinge connecting proximal ends of the first and second lateral members, and first and second press tabs for moving the first and second lateral members about the living hinge. The first lateral member and the first press tab are in an opposed and spaced-apart relationship to the second lateral member and second press tab, respectively. To open and close the lateral members, at least one of the press tabs pivots about the living hinge away from and toward the other press tab. The holder can include one or more retaining walls to inhibit lateral movement of the sensor when positioned between the first and second lateral members.

27 Claims, 7 Drawing Sheets

DISPOSABLE SENSOR HOLDER

FIELD OF THE INVENTION

The present invention relates generally to photoplethysmographic measurement instruments such as an oximeter and more particularly to disposable and/or reusable holders for disposable sensors.

BACKGROUND OF THE INVENTION

A common method used to identify problems with a patient's respiratory and/or circulatory system is oximetry. The color of the blood (i.e., the amounts of red and infrared radiation absorbed by the blood) is a function of the oxygen saturation of the heme in the blood's hemoglobin. For example, heme that is saturated with oxygen appears bright red because saturated heme is highly permeable to red light. In contrast, heme that is deoxygenated appears dark and bluish as it is less permeable to red light.

An oximeter sensor, particularly a pulsed oximeter sensor, includes one or more emitters for irradiating arterial blood of the patient with red and infrared radiation and a detector for measuring the corresponding amounts of the red and infrared radiation that are not absorbed by the heme in the blood. The sensor can be attached to a sensor holder which attaches or clips the sensor onto a body part for performing the oxygen saturation measurement.

There are a number of considerations in designing a holder for a pulsed oximeter sensor. The holder should be relatively inexpensive, simple to use, separate from the sensor (especially for disposable sensors), align the sensor in the holder for attachment to the body part, have the ability to immovably fix the sensor in position on the body part and thereby provide a reliable contact between the patient's skin and the faces of the emitter and detector (to increase the signal-to-noise ratio of the sensor output signals), capable of being used in a variety of body parts on the patient, disposable or reusable as desired, and capable of ready application to and removal from the patient with a small amount of discomfort and pain.

SUMMARY OF THE INVENTION

It is an objective of the present invention to provide an inexpensive holder for a sensor and/or a sensor holder that is relatively simple to use. Related objectives are to provide a sensor holder that is separate from the sensor, aligns the sensor in the holder for attachment to the body part, substantially restricts movement of the sensor on the body part, provides a reliable contact between the patient's skin and the faces of the emitter and detector of the sensor, is capable of being used on a variety of body parts on the patient, both disposable and reusable and/or can be readily applied to and removed from the patient with a small amount of discomfort and pain.

These and other objectives are addressed by the sensor holder of the present invention. The sensor holder is discrete from the sensor and includes: (i) first and second lateral members for receiving the sensor; (ii) a hinge member connecting proximal ends of the first and second lateral members; and (iii) first and second press tabs for moving the first and second lateral members about the hinge. The movement of the lateral members permits the holder to attach to and form a reliable sensor interface with body parts having a wide range of sizes and/or various locations on the same body part. The first press tab extends from the proximal end of the first lateral member, and the second press tab extends from the proximal end of the second lateral member. Thus, the lateral members each extend towards the distal end of the holder and the press tabs towards the proximal end. The first lateral member and the first press tab are positioned opposite the second lateral member and second press tab, respectively. To open and close the lateral members, at least one of the press tabs can pivot about the hinge member away from and towards the other press tab. This feature provides for ease and simplicity of use, particularly in attaching the holder to body parts of varying sizes.

The sensor holder offers a number of other advantageous features. The holder can be relatively inexpensive. This is due in part to the fact that the sensor holder can be of a one-piece or single-molded construction, which requires little or no assembly time to manufacture. Because the holder can be relatively inexpensive, the holder can be disposable or reusable, as desired. The hinge member can be advantageously constructed to define a "living hinge." As will be appreciated, a living hinge is a nonmechanical hinge generally formed from single-molded plastic. For a given displacement of the lateral members relative to one another, the living hinge can exert a substantially constant and moderate force on the body part, thereby immovably fixing the sensor in position on the body part and providing a firm contact between the skin and the emitter and detector of the sensor. The use of the hinge member to apply a moderate force to the body part via the lateral members permits the sensor holder to be readily applied to and removed from the patient with a minimum amount of discomfort and/or pain. The living hinge can obviate the need for adhesives and other bonding substances to realize a reliable contact. The arcuate shape of the living hinge minimizes stress on the various sensor components by alleviating sharp bends in the sensor when attached to the sensor holder.

The first and second lateral members can include a number of features to align the sensor in the holder, retain the sensor in the holder, and/or inhibit lateral and longitudinal movement of the sensor in the holder. By way of example, to align the sensor in the holder and inhibit lateral movement of the sensor in the holder, the lateral members can include (i) one or more raised steps to engage one or more edges of the sensor and/or a slot for receiving a portion of the sensor to maintain the sensor in a stationary relationship relative to the center axes of the lateral members (i.e., to inhibit movement of the sensor relative to the lateral members in a plane transverse to the plane of movement of the lateral members) and/or (ii) one or more pockets for receiving one or more ends of the sensor to maintain the sensor in a face-to-face relationship with the lateral members (i.e., to inhibit movement of the sensor relative to the lateral members in the plane of movement of the lateral members).

The step can be located on a peripheral edge of one or both of the lateral members. These features maintain the detector and emitters in proper alignment relative to one another, inhibit the formation of gaps between the detector and/or emitters and the body part, and inhibit movement of the detector and/or emitters relative to the body part to provide a reliable blood oxygen saturation measurement. To retain the sensor in the holder the first and second lateral members can engage the sensor in a face-to-face relationship. The face-to-face relationship can be on the exterior or interior surfaces of the lateral members.

To provide a simple design for the holder, the first and second press tabs and first and second lateral members can move in substantially parallel planes. Thus, the first press tab moves relative to the second press tab in a first plane, and the first lateral member moves relative to the second lateral member in a second plane. The first and second planes are substantially parallel. The use of substantially parallel planes of movement simplifies the application and removal of the sensor holder relative to the body part.

To provide for ease of use and a reliable contact between the sensor and the body part, the longitudinal center axis of the sensor can be aligned with the longitudinal center axes of the lateral members and/or the longitudinal center axes of the press tabs. Thus, the center axes of the sensor and lateral members and/or press tabs can define a common plane.

DETAILED DESCRIPTION

Figure 8:
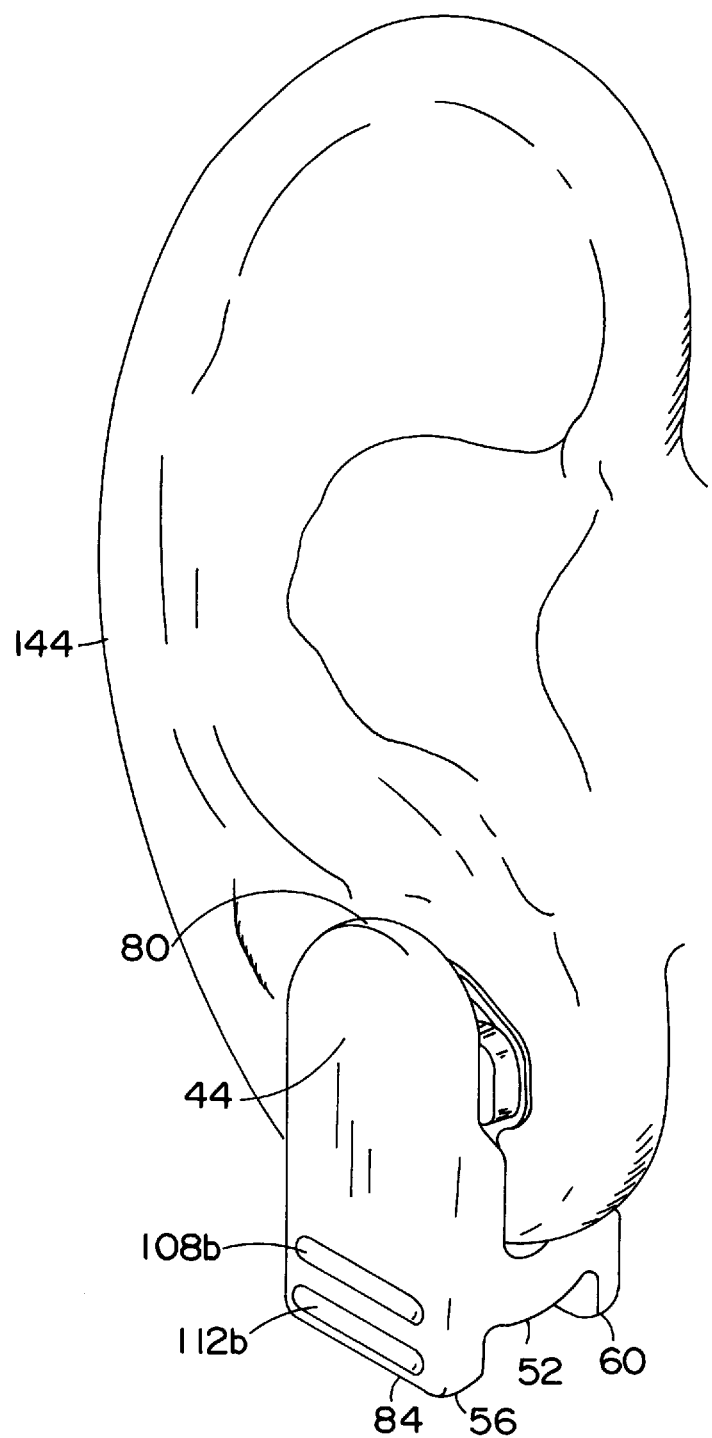
FIG. 8 depicts the sensor holder attached to a body art (i.e., an ear)
Figure 9:
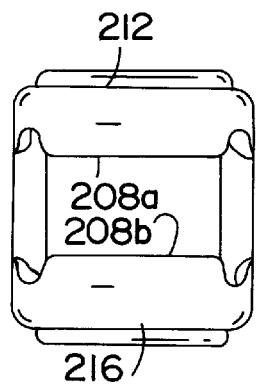
FIGS. 9–11 depict two configurations of another embodiment of the sensor holder according to the present invention.
Figure 10:
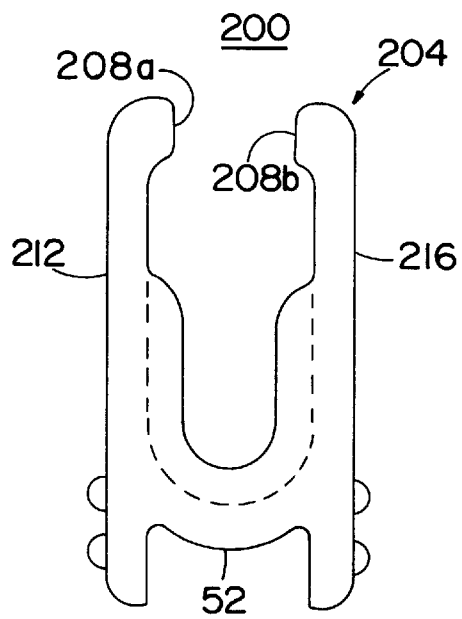
Figure 11:
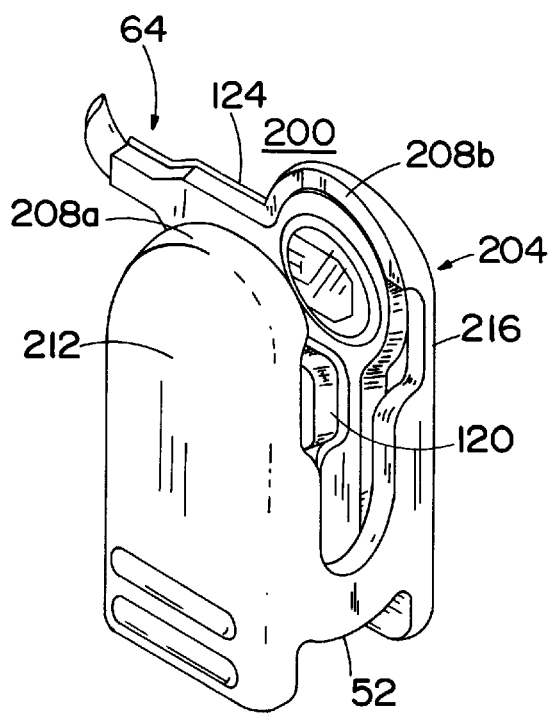
Figure 12:
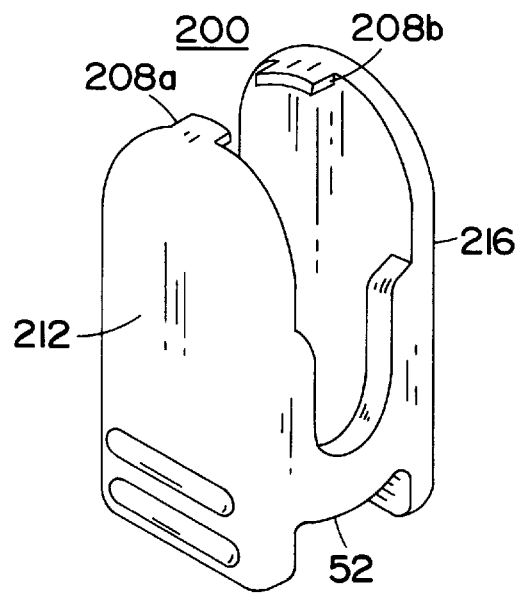
FIGS. 12–14 depict another embodiment of the sensor holder according to the present invention.
Figure 13:
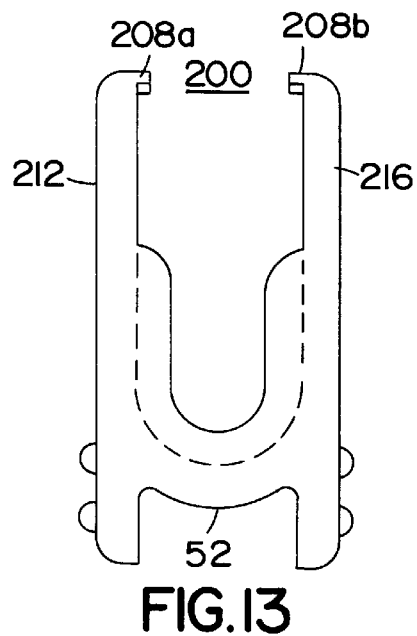
Figure 14:
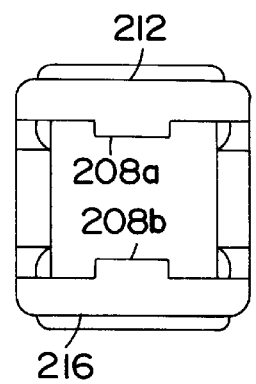

Referring to FIGS. 1–4, the sensor holder 40 according to one embodiment of the present invention includes first and second lateral members 44 and 48, a hinge member 52, and first and second press tabs 56 and 60. As shown in FIG. 8, a sensor 64, which includes a sensor housing 68, emitters 72a,b, and a detector 76, is received between the first and second lateral members 44 and 48 and attached to a body part, such as an ear lobe, fingertip, and the like.

The first and second lateral members 44 and 48 project towards the distal end 80 of the sensor holder 40).

The lateral members 44 and 48 are in an opposed and spaced apart relationship to receive the sensor 64 between the lateral members. The distance "d" between the lateral members housing a sensor when the holder is in the closed or neutral position (i.e., relaxed position) is less than the thickness of the body part to which the sensor assembly 40 is to be attached. In the closed position, the interior and exterior surfaces 88a,b and 92a,b of the lateral members may be angled towards one another by an angle "θ" (measured from a longitudinal center plane 96 of the sensor holder). Thus, when in the closed or neutral position the interior and exterior surfaces 88a,b and 92a,b are not mutually parallel to one another but are transverse to the longitudinal center plane 96 of the sensor holder 40. The angle "θ" is preferably ranges from about −15 degrees and more preferably from about −2 to about −6 degrees. The interior and exterior surfaces 88a, b and 92a,b are spaced apart such that they are substantially parallel when the sensor holder 40 is attached to a body part.

The hinge member 52 is located or nested between the lateral members 44 and 48. The hinge member 52 is a living hinge. Living hinges are discussed in detail in U.S. Pat. No. 5,414,911 entitled "One-Piece Clamp-Type Clip" to Adams, which is incorporated fully herein by this reference. The living hinge is generally a one-piece nonmechanical hinge that automatically recloses to the closed position. Living hinges generally have an arcuate surface with a relatively large radius of curvature to distribute stress on the hinge over a relatively large surface area.

The press tabs 56 and 60 project towards the proximal end 84 of the sensor holder 40. The press tabs 56 and 60 are in an opposed and spaced apart relationship. In the closed position, the interior and exterior surfaces 100a,b and 104a,b of the press tabs are angled towards one another. The thickness "t" of each of the press tabs 56 and 60 is greater than the thickness "t" of the hinge member 52 so that movement of the press tabs 56 and 60 causes the lateral members 44 and 48 to open and close. As will be appreciated, if the hinge member 52 were to be thicker than the press tabs 56 and 60, the press tabs 56 and 60 would deform elastically and then plastically before elastic deformation of the hinge member 52 in response to a force applied to the press tabs by a user.

Figure 2:
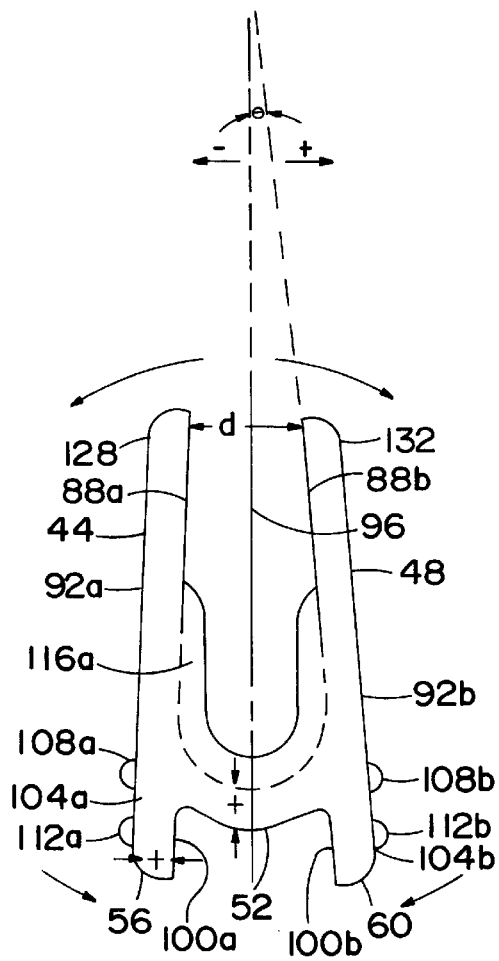
FIG. 2 is a side view of the embodiment of FIG. 1.
Figure 3:
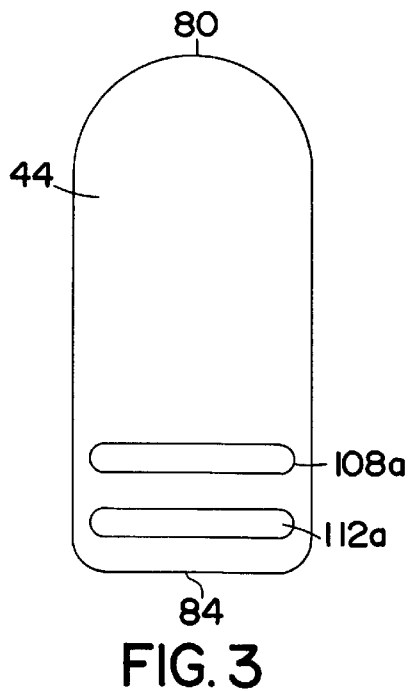
FIG. 3 is a side view of the embodiment of FIG. 1 taken along a different axis than that of FIG. 2.
Figure 5:
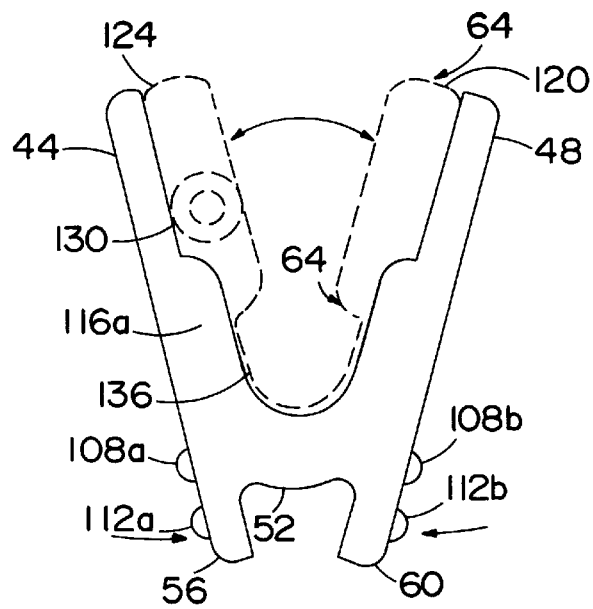
FIG. 5 is a side view of the embodiment of FIG. 1 taken along the same axis as FIG. 2 with the sensor holder in an open position.
Figure 6:
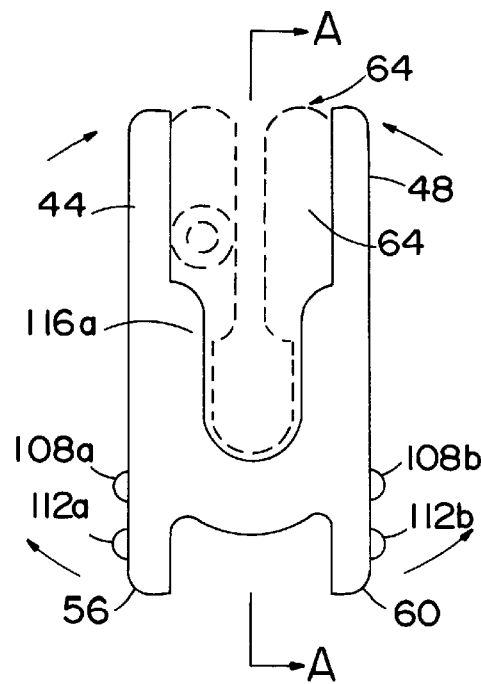
FIG. 6 is a side view of the embodiment of FIG. 1 taken along the same axis as FIG. 2 with the sensor holder in a closed position.

As shown in FIGS. 2 and 5–6, the lateral members 44 and 48 and press tabs 56 and 60 move in substantially parallel planes and are symmetrical about the longitudinal center plane 96. The relative directions of motion of the lateral members 44 and 48 and press tabs 56 and 60 are illustrated in FIGS. 5 and 6. When the press tabs 56 and 60 are moved closer together, the lateral members 44 and 48 are moved further apart, and when the press tabs 56 and 60 are moved further apart, the lateral members 44 and 48 are moved closer together.

Referring to FIGS. 2 and 5–6, each of the press tabs include a plurality of grips 108a,b and 112a,b for the convenience of the user. The grips 108 and 112 are raised areas or ridges on the exterior surfaces 104a,b of the press tabs 56 and 60 that increase the force of friction between the user's fingers and the surfaces to provide better gripping of the press tabs 56 and 60.

Figure 1:
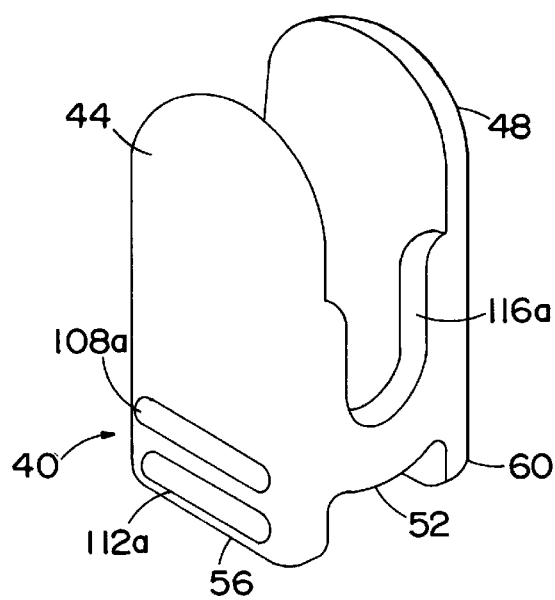
FIG. 1 is a perspective view of an embodiment of a sensor holder according to the present invention.
Figure 4:
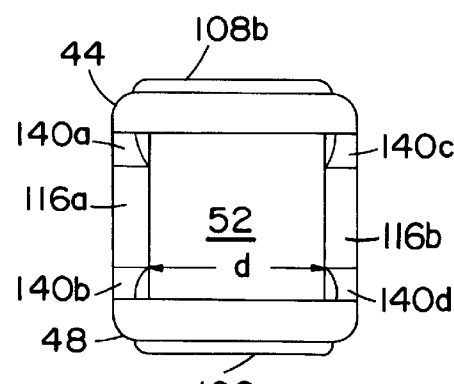
FIG. 4 is a front view of the embodiment of FIG. 1.
Figure 7:
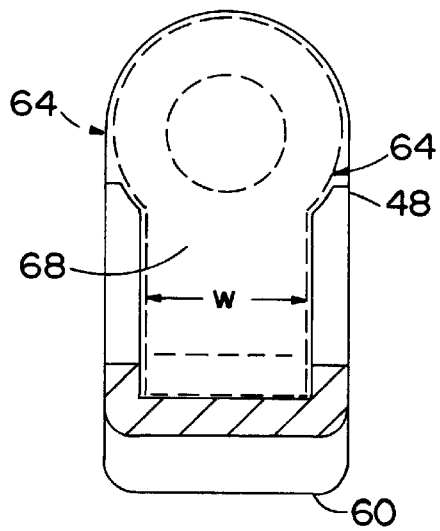
FIG. 7 is a cross-sectional view taken along line A—A FIG. 6.

Referring to FIGS. 1–2 and 4, the peripheral edges of the lateral members and hinge member can include retaining walls 116a,b to inhibit lateral motion of the sensor 64 when received between the lateral members 44 and 48 and to retain the sensor 64 between the lateral members 44 and 48. Each of the retaining walls 116a,b can be continuous as shown or discontinuous along the length of the interior surfaces 88a,b of the lateral members and the interior surface of the hinge member. Referring to FIGS. 4 and 7, the distance "d" between the retaining walls 116a,b is substantially the width "w" of the portion of the sensor housing 68 that is received between the walls. Referring to FIG. 2, the retaining walls 116a,b extend only part of the distance from the hinge member 52 to the distal end 80 of the holder to permit the opposing ends 120 and 124 of the sensor to be positioned in the distal portions 128 and 132 of the lateral members 44 and 48. The opposing ends 120 and 124 of the sensor are larger than the central portion 136 of the sensor housing which is received between the retaining walls 116a,b. The positioning of the emitters and detectors adjacent to the interior surfaces of the first and second lateral members provides a reliable contact between the emitters and detector on the one hand and the patient's skin on the other. Referring to FIG. 4, the ends 104a–d of the retaining walls are flared outwardly to conform to the circular shape of the opposing ends 120 and 124 of the sensor.

The sensor holder 40 can be composed of any suitable deformable material, with plastics such as polycarbonate, pc/abs blend, and nylon. Plastic is relatively inexpensive and can be converted by a number of low cost and high volume processes, such as injection molding, into articles, such as the holder. The sensor holder 40 is of a one-piece molded construction. The dimensions of the sensor holder depend, of course, on the dimensions of the sensor.

Referring to FIGS. 5–8, the operation of the sensor holder 40 will now be described with reference to an ear lobe. As will be appreciated, the steps are equally applicable to other body parts, such as a finger.

To place the sensor 64 in a nested relationship between the lateral members 44 and 48, the press tabs 56 and 60 are moved closer together, thereby causing the lateral members 44 and 48 to move further apart to the open position (shown in FIG. 5). In this position, the lateral members 44 and 48 are transverse to one another at an angle "0" ranging from about 20 to about 45 degrees. An adhesive substance can be placed in the distal portions 128 and 132 of the interior surfaces 88a,b to bond the opposing ends 120 and 124 to the respective interior surface. The sensor 64 is then placed in a face-to-face relationship with the interior surfaces of the lateral members 44 and 48 and the hinge member 52 such that the sensor housing is positioned between the retaining walls 116a,b and the opposing ends 120 and 124 of the sensor 64 are located in the distal portions 128 and 132 of the interior surfaces of the lateral members. For the best contact between the emitters and detector on the one hand and the skin on the body part 144 on the other, it is important for the opposing ends 120 and 124 of the sensor 76 to be in a face-to-face relationship with the distal portions 128 and 132 of the interior surfaces of the lateral members. The interface between the rear surface 130 of the sensor housing and the interior surfaces of the first and second lateral members and hinge member is substantially planar (i.e., flat).

Following insertion of the sensor 64 between the lateral members 44 and 48, the body part 144 is placed between the opposing ends 120 and 124 of the sensor 64 and the pressure applied to the press tabs 56 and 60 is gradually reduced until the body part 144 is firmly held between the opposing ends 120 and 124. At this point, the press tabs 56 and 60 are released by the user. The interior and exterior surfaces of the first and second lateral members are substantially parallel to one another and to the longitudinal center plane 96 to provide a more reliable interface between the emitters and detectors on the one hand and the skin of the body part on the other.

After the sensor 64 is clipped onto the body part 144, the oxygen saturation of the blood can be measured by energizing the emitters to produce a spectral content and detecting the unabsorbed radiation as noted above.

The sensor 64 and sensor holder 40 can be disposed of or reused as desired. If reused, the sensor holder 40 is thermally and/or chemically sterilized in a suitable device, such as an autoclave. A new or sterilized sensor 64 can be used with the sterilized sensor holder 40.

Alternative configurations of another embodiment of the sensor holder according to the present invention is illustrated in FIGS. 9–14. The distal end 200 of the sensor holder 204 has retaining teeth 208a,b at the peripheral edges of the lateral members 212 and 216 for engaging the opposing ends 120 and 124 of the sensor 64. The teeth 208a,b can be flared outwardly to receive the circularly shaped opposing sensor ends 120 and 124. The teeth 208a,b hold the sensor 64 firmly in a face-to-face relationship with the hinge member 52 and lateral members 212 and 216 and prevent the sensor 64 from moving away from the sensor holder 204 towards the holder's distal end 200.

Figure 15:
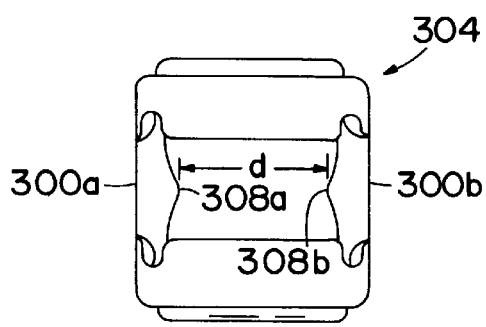
FIG. 15 depicts another embodiment of the sensor holder according to the present invention.
Figure 16:
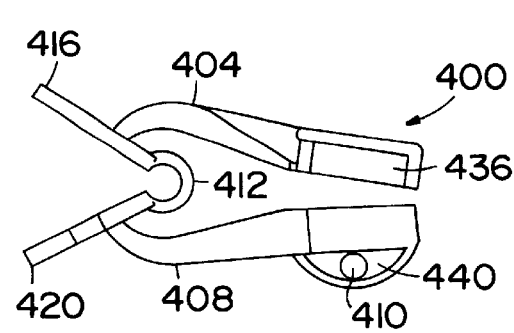
FIG. 16 is a top view of another embodiment of the sensor holder according to the present invention.
Figure 17:
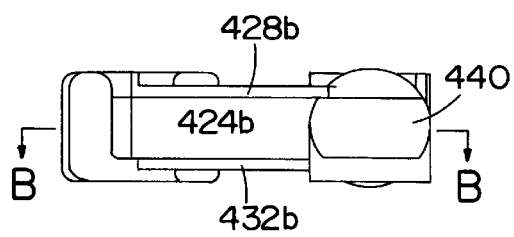
FIG. 17 is a side view of the sensor holder of FIG. 16.

Yet another embodiment of the sensor holder according to the present invention is depicted in FIG. 15. One or both of the retaining walls 300a,b of the holder 304 include a dimple 308a,b projecting inwardly to pinch the central portion 136 of the sensor housing 68 and thereby hold the sensor 64 firmly in position in the holder 304. As will be appreciated, the distance "d" between the dimples 308a,b is slightly less than the width "w" (see FIG. 7) of the actual portion of the sensor housing at the point at which the sensor housing is received between the dimples.

Figure 18:
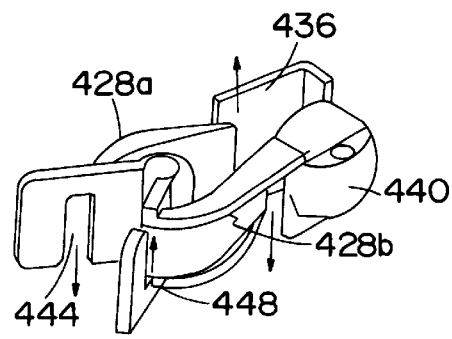
FIG. 18 is a perspective view of the sensor holder of FIG. 16.
Figure 19:
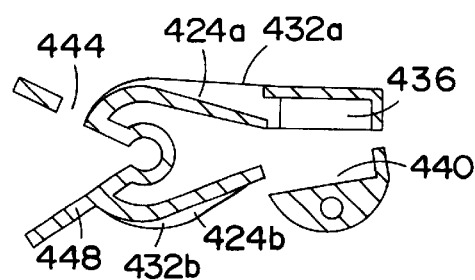
FIG. 19 is a cross-sectional view of the sensor holder of FIG. 16 taken along line B—B of FIG. 17.

A further embodiment of the holder according to the present invention is depicted in FIGS. 16–19. The holder 400 includes first and second lateral members 404 and 408, a hinge member 412, and press tabs 416 and 420. Each of the lateral members 404 and 408 includes a continuous channel 424a,b formed by spaced apart and opposing retaining walls 428a,b and 432a,b for receiving the central portion 136 of the sensor housing 68 and one or more pockets 436 and 440 for receiving the opposing ends 120 and 124 of the sensor 64. As shown in FIG. 18, the pockets 436 and 440 open in opposite directions to firmly hold the sensor 64 in a face-to-face relationship with the channels in the lateral members 404 and 408. Each of the press tabs 416 and 420 include oppositely facing slots 444 and 448 for receiving the central portion 136 of the sensor housing 68 to provide further support for holding the sensor 64 in a face-to-face relationship with the channels in the lateral members 404 and 408. A stabilizer (not shown), such as an earprobe stabilizer (i.e., a loop that wraps around an ear) sold under the tradename "OHMEDA, INC. PN 7700-025 (0380-0100-182), can be attached to the hole 410 and be hooked over the ear to stabilize the sensor holder on the body part.

Figure 20:
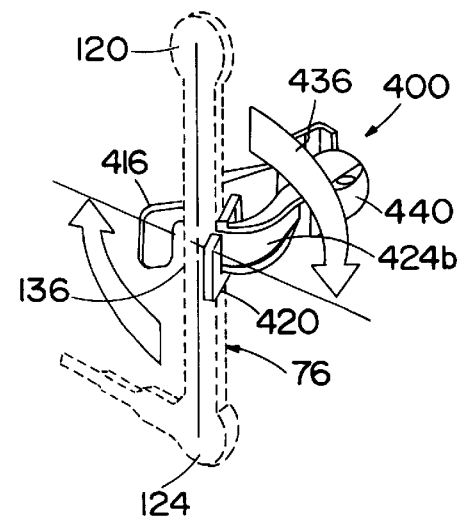
FIGS. 20–22 are views of the sensor holder of FIG. 16 engaging a sensor assembly.
Figure 21:
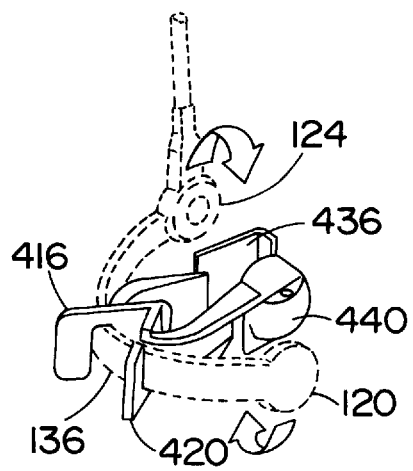

The method for using the sensor holder 400 will now be described with reference to FIGS. 20–22. When the sensor holder 400 is in the closed position the sensor 64 is rotated from an upright position to a position in which the central portion 136 of the sensor housing is aligned with the channels 424a,b. The opposing ends 120 and 124 are placed in the appropriate pocket 440 or 436 and the central portion 136 of the housing in the channels 424a,b.

Figure 22:
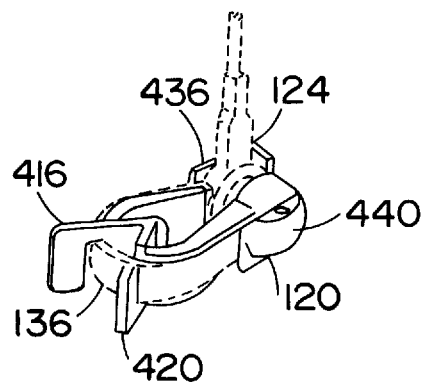

After placing the sensor 64 in the sensor holder 400 as shown in FIG. 22, the sensor holder 400 is opened by forcing the press tabs 416 and 420 closer to one another, which causes the lateral members 404 and 408 to move further apart, the body part is placed between the opposing ends 120 and 124 of the sensor 64, and the press tabs 416 and 420 gradually released until the body part is firmly gripped between the opposing ends 120 and 124 of the sensor 64.

Figure 23:
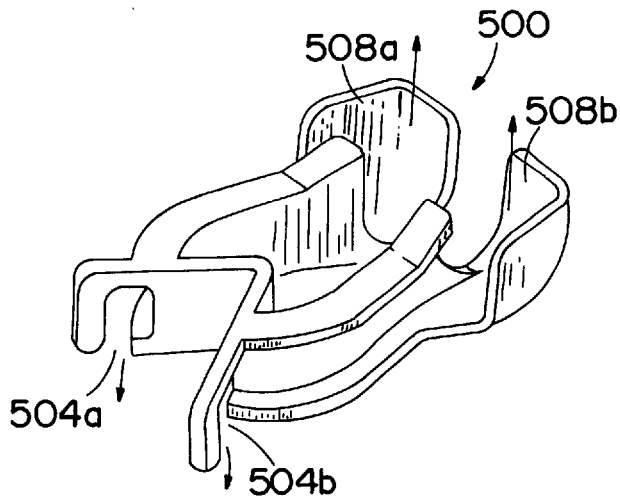
FIG. 23 is a perspective view of a sensor holder according to yet another embodiment of the present invention.
Figure 24:
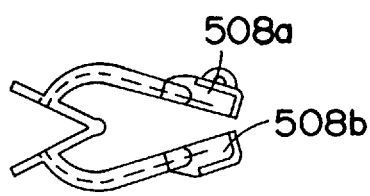
FIG. 24 is a top view of the sensor holder of FIG. 23.
Figure 25:
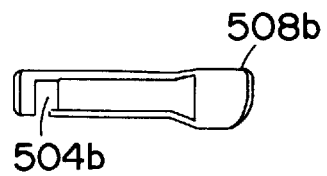
FIG. 25 is a side view of the sensor holder of FIG. 24.

Yet another embodiment is depicted in FIGS. 23–25. The holder 500 differs from the holder 400 of the previous embodiment in that the pair of slots 504a,b open in the same directions and the pair of pockets 508a,b open in the same directions. However, the pair of slots 504a,b open in the opposite direction from the pair of pockets 508a,b.

While various embodiments of the present invention have been described in detail, it is apparent that modifications and adaptations of those embodiments will occur to those skilled in the art. For example, it should be appreciated that the retaining walls can be discontinuous and/or can extend around all or substantially all of the outer perimeter of the hinge member and lateral members depending upon the design of the sensor. These variations are all considered to fall within the scope of the present invention. Therefore, it is to be expressly understood that such modifications and adaptations are within the spirit and scope of the present invention, as group forth in the following claims.

What is claimed is:

1. A holder for a discrete, flexible sensor for monitoring an animate body, comprising:

first and second lateral members for receiving the sensor, the first and second lateral members being positioned in an opposing relationship relative to one another and extending towards a distal end of the holder;

a hinge member connecting a first end of the first lateral member to a second end of the second lateral member, said hinge member having an inwardly facing surface and an outwardly facing surface, wherein at least one of the inwardly and outwardly facing surfaces is arcuate in configuration for receiving at least a portion of the sensor in a face to face relationship;

first and second press tabs for moving the first and second lateral members, the first press tab depending from the first end of the first lateral member and the second press tab depending from the second end of the second lateral member, the first and second press tabs extending towards the proximal end of the holder and being positioned in an opposing relationship relative to one another, wherein at least one of the first and second press tabs is pivotable about the hinge member so as to be movable between a distal first position and a proximal second position relative to the other of the first and second press tabs to move at least one of the first and second lateral members between a proximal first position and a distal second position relative to the other of the first and second lateral members wherein the first press tab and the first lateral member move relative to one another in at least one of the same plane and parallel planes, and the second press tab and the second lateral member move relative to one another in at least one of the same plane and parallel planes.

2. The holder of claim 1, wherein the first and second lateral members are adapted to engage in a face-to-face relationship with the sensor when the sensor is received by the first and second lateral members.

3. The holder of claim 2, wherein the first lateral member has a first surface and the second lateral member has a second surface in an opposing relationship to the first surface, the first and second surfaces facing the distal end, and wherein the face-to-face relationship is between one of the first and second surfaces and a surface of the received sensor.

4. The holder of claim 1, wherein the first lateral member includes a first surface and the second lateral member has a second surface and a portion of at least one of the first and second surfaces is raised relative to at least one adjacent portion of the at least one of the first and second surfaces to engage an edge of the sensor and to inhibit lateral movement of the sensor when the sensor is received by the first and second lateral members.

5. The holder of claim 4, wherein the portion is formed by a peripheral edge of at least one of the first and second surfaces.

6. The holder of claim 4, wherein the edge is an end of the received sensor.

7. The holder of claim 4, wherein the edge is a side of the received sensor.

8. The holder of claim 1, wherein the hinge member is a living hinge.

9. The holder of claim 8, wherein the first and second press tabs have first and second thicknesses, respectively, and the hinge member has a third thickness, each of the first and second thicknesses being greater than about the third thickness.

10. The holder of claim 1, wherein the hinge member is nonmechanical.

11. The holder of claim 1, wherein the holder is a single-molded part.

12. The holder of claim 1, wherein the holder is of a one-piece construction.

13. The holder of claim 1, wherein the first and second lateral members and hinge member form a continuous, arcuate surface.

14. A holder for a flexible sensor for monitoring an animate body, comprising:

first and second lateral members for receiving the sensor, the first and second lateral members being positioned in an opposing relationship relative to one another, the first and second lateral members extending towards a distal end of the holder;

a hinge member connecting a first end of the first lateral member to a second end of the second lateral member;

first and second press tabs for moving the first and second lateral members, the first press tab depending from the first end of the first lateral member and the second press tab depending from the second end of the second lateral member, the first and second press tabs extending towards the proximal end of the holder and being positioned in an opposing relationship relative to one another, wherein at least one of the first and second press tabs pivots about the hinge member to cause (i) the at least one of the first and second press tabs to move in a first plane between a distal first position and a proximal second position relative to the other of the first and second press tabs and (ii) at least one of the first and second lateral members to move in a second plane between a proximal first position and a distal second position relative to the other of the first and second lateral members, the first and second planes being substantially parallel wherein, at least one of the first and second press tabs includes at least a first slot adapted for receiving and aligning a portion of the sensor when the sensor is received by the first and second lateral members.

15. The holder of claim 14, wherein the first and second lateral members and hinge member form an arcuate surface adapted for receiving at least a portion of the sensor in a face to face relationship when the sensor is received.

16. The holder of claim 14, wherein the first and second press tabs each include an exterior surface, the exterior surface of at least one of the first and second press tabs including at least one raised portion for facilitating gripping of the holder, wherein the at least one raised portion is raised relative to adjacent portions of the exterior surface.

17. The holder of claim 14, wherein the holder is adapted to receive a part of an animate body between the first and second lateral members, the received part of the animate body being non-adhesively engaged by the holder.

18. The holder of claim 14, wherein the distal ends of the first and second lateral members are in a non-overlapping relationship relative to one another.

19. The holder of claim 14, wherein the first press tab includes the first slot and the second press tab includes a second slot, the first and second slots each being adapted for receiving and aligning a portion of the sensor when the sensor is received by the first and second lateral members and wherein, the first slot opens upwardly and the second slot opens downwardly.

20. The holder of claim 14, wherein a distal end of at least one of the first and second lateral members includes a pocket configured for receiving an end of the sensor when the sensor is received by the first and second lateral members.

21. The holder of claim 14, wherein a distal end of the first lateral member includes a first pocket and a distal end of the second lateral member includes a second pocket, the first and second pockets each being capable of receiving an end of the sensor when the sensor is received by the first and second lateral members, and wherein, the first and second pockets open in different directions.

22. A holder for a flexible sensor for monitoring an animate body, the sensor including an emitter and a detector contained within a sensor housing, comprising:

first and second lateral members for receiving the sensor, the first and second lateral members being positioned in an opposing relationship relative to one another, the first and second lateral members extending towards a distal end of the holder;

a hinge member connecting a first end of the first lateral member to a second end of the second lateral member;

first and second press tabs for moving the first and second lateral members, the first press tab depending from the first end of the first lateral member and the second press tab depending from the second end of the second lateral member, the first and second press tabs extending towards the proximal end of the holder and being positioned in an opposing relationship relative to one another, wherein at least one of the first and second press tabs pivots about the hinge member to cause (i) the at least one of the first and second press tabs to move in a first plane between a distal first position and a proximal second position relative to the other of the first and second press tabs and (ii) at least one of the first and second lateral members to move in a second plane between a proximal first position and a distal second position relative to the other of the first and second lateral members, the first and second planes being substantially parallel, wherein at least one of the first and second lateral members has a raised portion for engaging the sensor to inhibit transverse movement thereof relative to a longitudinal center axis of said at least one of the first and second lateral members when said sensor is received between said lateral members.

23. The holder of claim 22, wherein each of the first and second lateral members has a raised portion.

24. The holder of claim 22, wherein a first raised portion is located adjacent to one side of at least one of the first and second lateral members and a second raised portion is located adjacent to the other side of the at least one of the first and second lateral members.

25. The holder of claim 22, wherein the hinge member has a second raised portion to contact the sensor when the sensor is received by the first and second lateral members.

26. The holder of claim 22, wherein the raised portion is located near the hinge member.

27. The holder of claim 22, wherein the raised portion extends in a direction parallel to the longitudinal center axis of said at least one of the first and second lateral members to restrict transverse movement of the sensor relative to the longitudinal center axis of said at least one of the first and second lateral members.

* * * * *